United States Patent
Arnason et al.

(10) Patent No.: US 9,386,767 B2
(45) Date of Patent: Jul. 12, 2016

(54) DERIVATIVES OF DILLAPIOL AND RELATED MONOLIGNANS AND USE THEREOF

(75) Inventors: John Thor Arnason, Ottawa (CA); Tony Durst, Ottawa (CA); Brian Foster, Nepean (CA)

(73) Assignees: UNIVERSITY OF OTTAWA, Ottawa (CA); HER MAJESTY THE QUEEN IN RIGHT OF CANADA, AS REPRESENTED BY THE MINISTER OF HEALTH, Ottawa (CA)

( * ) Notice: Subject to any disclaimer, the term of this patent is extended or adjusted under 35 U.S.C. 154(b) by 653 days.

(21) Appl. No.: 13/469,870

(22) Filed: May 11, 2012

(65) Prior Publication Data

US 2013/0012477 A1     Jan. 10, 2013

Related U.S. Application Data

(60) Provisional application No. 61/484,809, filed on May 11, 2011.

(51) Int. Cl.
*A01N 43/30* (2006.01)
*C07D 317/54* (2006.01)
*A01N 53/00* (2006.01)
*C07D 317/64* (2006.01)
*C07D 317/68* (2006.01)

(52) U.S. Cl.
CPC .............. *A01N 43/30* (2013.01); *C07D 317/54* (2013.01); *C07D 317/64* (2013.01); *C07D 317/68* (2013.01)

(58) Field of Classification Search
None
See application file for complete search history.

(56) References Cited

PUBLICATIONS

Majerus et al. (Canadian Journal of Chemistry, 78 (10): 1345-1355, 2000).*
Majerus (University of Ottawa Theses, 1997).*
Belzile et al., "Dillapiol derivatives as synergists: structure-activity relationship analysis." Pest. Biochem Physiol. 66 (1):33-40 (2000).
Budzinski et al, "An in vitro evaluation of human cytochrome P450 3A4 inhibition by selected commercial herbal extracts and tinctures." Phytomedicine 7(4):273-282 (2000).
Flentge et al., . "Synthesis and evaluation of inhibitors of cytochrome P450 3A (CYP3A) for pharmacokinetic enhancement of drugs." Bioorg. Med. Chem. Lett. 19(18):5444-5448 (2009).
Foster et al., "Comparative study of hops-containing products on human cytochrome P450-mediated metabolism." J. Agric. Food Chem. 59(9):5159-5163 (2011).
Omar et al., "Antimalarial activities of gedunin and 7-methoxygedunin and synergistic activity with dillapiol." Ann. Appl. Biol 143(2):135-141 (2003).
Strunz et al., "Synthesis of sarmentosine, an amide alkaloid from Piper sarmentosum." Phytochemistry 39(3):731-733 (1995).
Wagemann et al., "Functionalized chloroenamines in aminocyclopropane synthesis—XIV. Aminoannulated cyclopropanes—rigid building blocks for oligoamines." Tetrahedron 50(3):731-748 (1994).
Wynn et al., "Sesamol as an inhibitor of growth and lipid metabolism in Mucor circinelloides via its action on malic enzyme." Lipids 32(6):605-610 (1997).
Ohsawa "Sesamol and sesaminol as antioxidants", New Food Industry, 33(6):1-5 (1991). (English Abstract Only).

* cited by examiner

*Primary Examiner* — Bong-Sook Baek
(74) *Attorney, Agent, or Firm* — Nixon Peabody LLP; David S. Resnick

(57) ABSTRACT

Derivatives of dillapiol, sesamol and related monolignans having the following general formula:

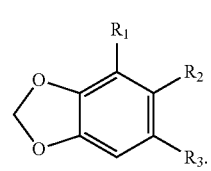

These compounds have synergistic properties, inhibit cytochrome P450 enzymes such as human CYP3A4, and can be used as pesticide synergists or pharmaco-enhancers. Accordingly, methods for increasing the efficacy and/or bioavailability of a pharmaceutically active agent and for increasing the potency of a pesticide are described, as are synergistic pesticidal and pharmaceutical compositions.

14 Claims, 2 Drawing Sheets

DERIVATIVES OF DILLAPIOL AND RELATED MONOLIGNANS AND USE THEREOF

CROSS REFERENCE TO RELATED APPLICATION

This application claims benefit under 35 U.S.C. §119(e) of U.S. Provisional Application No. 61/484,809 filed May 11, 2011, the contents of which are incorporated herein by reference in its entirety.

FIELD OF INVENTION

The present invention relates to synergistic compounds, including compositions comprising such compounds and methods of use thereof. The synergistic compounds are derivatives of dillapiol, sesamol and related monolignans and can be used to enhance the potency of certain pesticides and pharmaceuticals.

BACKGROUND OF THE INVENTION

Synergists are used to improve potency and reduce costs associated with expensive active principles, such as those used in pesticides and pharmaceuticals.

Dillapiol, a naturally occurring monoligan found in many plant families, has been demonstrated to act as a synergist. It has shown promise in the area of insecticidal activity, where co-administration of dillapiol with alpha-terthienyl, a photo-toxic larvicide, increased toxicity in mosquito larvae by a synergism factor of 1.9 (Belzile et al, 2000, Pest. Biochem. Physiol., 66:33-40). Synergism has also been demonstrated in vivo, where co-administration of dillapiol with the plant-derived antimalarial compound genudin increased parasitemia clearance in mice by 29% (Omar et al., 2003 Ann. Appl. Biol., 143(2):135-141). A mechanism for dillapiol's observed synergism is suggested by the observation that it inhibits the human cytochrome P450 3A4 (CYP3A4) enzyme, a key metabolic enzyme (Budzinski et al., 2000, Phytomedicine, 7(4):273-282).

The cytochrome P450s (CYPs) are an important family of enzymes responsible for many Phase I metabolic biotransformations. CYP3A4 is the most prominent member of the CYP family responsible for metabolism of more than 60% of all xenobiotics, such as pesticides and pharmaceuticals. Recently, there has been interest in inhibiting CYP3A4 to increase drug concentration and/or activity of active principles in the body. The effect of CYP inhibition is pharmaco-enhancement, where CYP3A4 inhibitors are co-administered, at sub-therapeutic levels, with a second active principle thereby synergistically increasing the activity of the second active principle. In this way a lower dose of the second active principle can be used to elicit the same therapeutic or inhibitory effect. This approach has been used with success in anti-HIV treatment where the CYP3A4 inhibitor ritonavir is paired with protease inhibitors in therapeutic drug "cocktails". Recently this enhancement has been extended with the synthesis of ritonavir derivatives that are more potent inhibitors and pharmaco-enhancers (Flentge et al., 2009, Bioorg. Med. Chem. Lett. 19(18):5444-5448).

Dillapiol has a long history of human food use since it constitutes about 30% of Indian Dill Oil, and is therefore generally recognized as safe (GRAS). Syntheses of dillapiol and several derivatives have been reported (Majeurus et al., 2000, Can. J. Chem. 78:1345-1355; Belzile et al, 2000, Pest. Biochem. Physiol., 66:33-40). However, none of these derivatives have been investigated as synergists for pyrethrins or other insecticides, or as potential pharmaco-enhancers.

Sesamol is a natural organic compound which is a component of sesame oil. Sesamol has been found to be an antioxidant that may prevent the spoilage of oils, and may protect the body from damage from free radicals (Ohsawa, Toshiko. "Sesamol and sesaminol as antioxidants" *New Food Industry* (1991), 33(6), 1-5). It also may prevent the spoilage of oils by acting as an antifungal (Wynn, James P.; Kendrick, Andrew; Ratledge, Colin. "Sesamol as an inhibitor of growth and lipid metabolism in *Mucor circinelloides* via its action on malic enzyme." *Lipids* (1997), 32(6), 605-610). Sesame oil is used in Ayur-Vedic Medicine.

Accordingly, there is considerable potential for dillapiol, derivatives derived from it and related monolignans as synergists in both the pesticide and pharmaceutical fields.

SUMMARY OF THE INVENTION

It is an object of the invention to provide derivatives of dillapiol, sesamol and other closely related monlignans which are useful as synergists, either as insecticide synergists or as pharmaco-enhancers.

According to an aspect of the present invention, there is provided a compound of formula I:

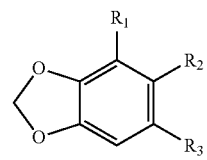

wherein $R_1$ is H, OH, OCH$_3$, CH$_2$OH, CH$_2$OCH$_3$, CHO, Br, SCH$_3$, or a group selected from CH(OH)C$_8$H$_{17}$, OC$_8$H$_{17}$, CH=CHCO$_2$CH$_3$, CH$_2$CH=CH$_2$, CH$_2$(O)CH$_2$CO$_2$C$_2$H$_5$, SO$_2$CH$_3$, S(O)CH$_3$, SPh, S(O)Ph, SO$_2$Ph, SC$_6$H$_4$pOCH$_3$; SO$_2$C$_6$H$_4$pOCH$_3$, SCH$_2$Ph, S(O)CH$_2$Ph, and SO$_2$CH$_2$Ph;

$R_2$ is OH, OCH$_3$, OCH$_2$Ph, or OCH$_2$R wherein R is a benzene ring substituted with one or more of F, Cl Br, methyl, methoxy or a 5- or 6-membered aromatic ring, $R_3$ is CH$_2$CH=CH$_2$, or a structure of the following type

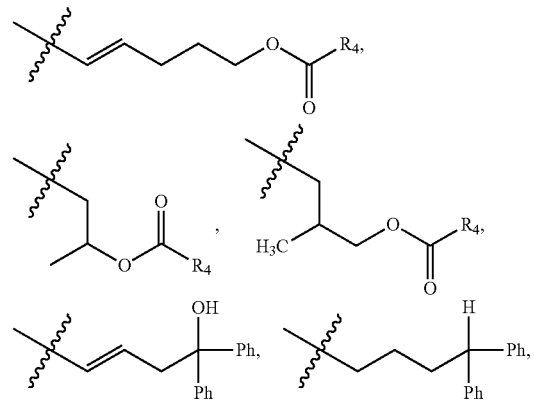

-continued

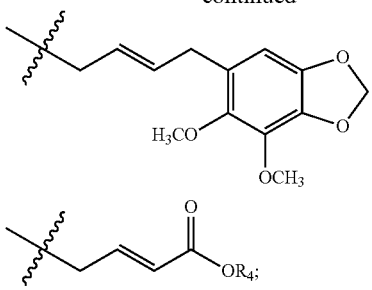

or

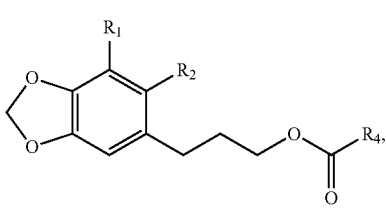

$R_4$ is $C_1$ to $C_6$ alkyl, $C_5$ to $C_6$ cycloalkyl, $C_2$ to $C_6$ alkenyl, aryl, $CH_2Ar$, $CH(CH_3)Ar$, or $CHAr_2$, in which aryl or Ar is unsubstituted phenyl (Ph), Ph mono or di-substituted with a halogen (such as but not limited to F and Cl), $CH_3$ or $OCH_3$, or a 5- or 6-membered hetero-aromatic ring, wherein heteroatoms in the ring include S, O or N;

or $R_2$ and $R_3$ together with the ring to which they are attached form a structure of the following type:

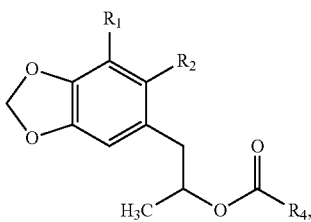

in which $R_4$ is as defined above;
including salts or esters thereof.

In certain embodiments, which may be preferred, the compound is of the formula II, III, IV, V, VI, VII, VIII or IX as follows:

II

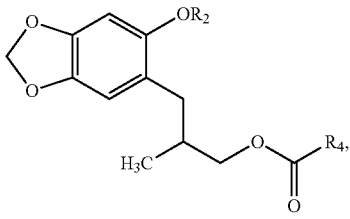

III

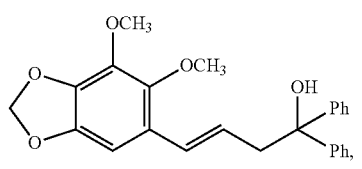

IV

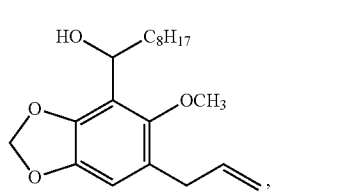

V

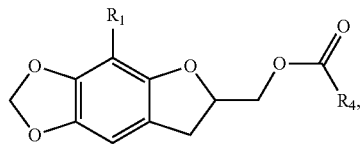

VI

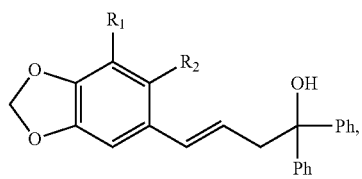

VII

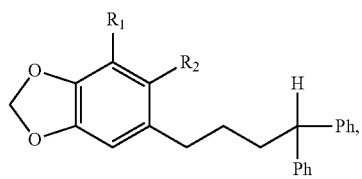

VIII

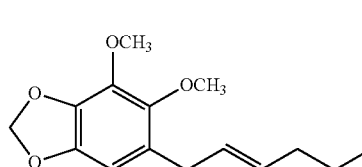

or

IX

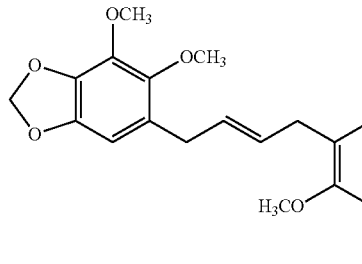

wherein $R_1$, $R_2$ and $R_4$ are as defined above, including salts or esters thereof.

In certain non-limiting embodiments of the invention the compound may have a molecular structure as shown in the following:

1

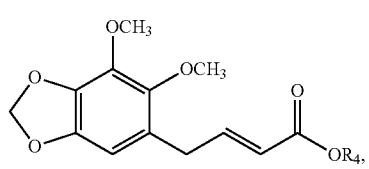

2

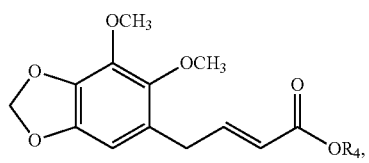

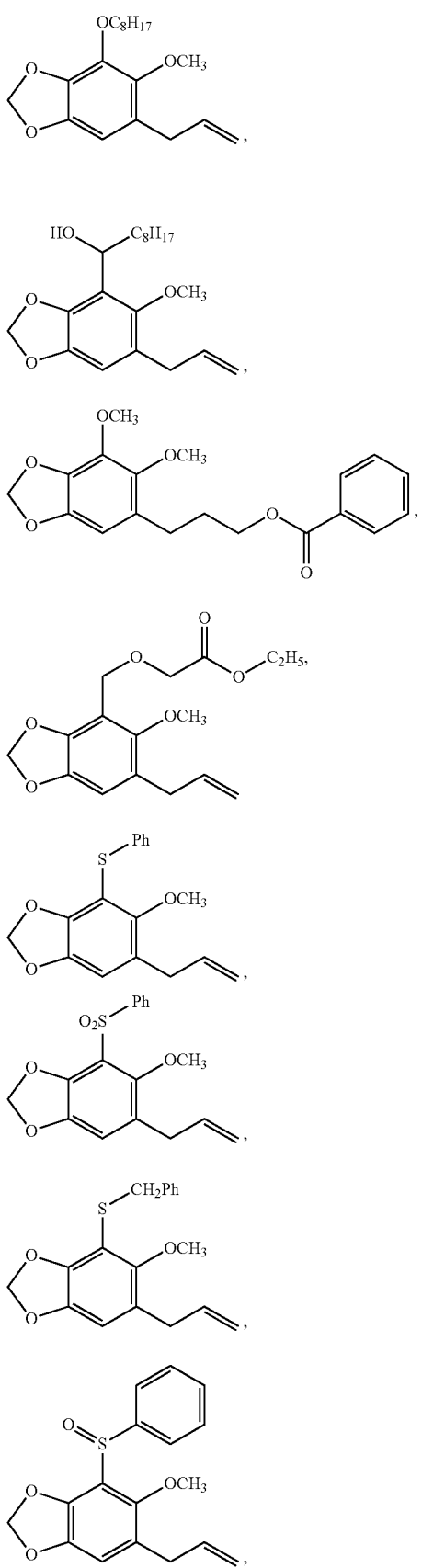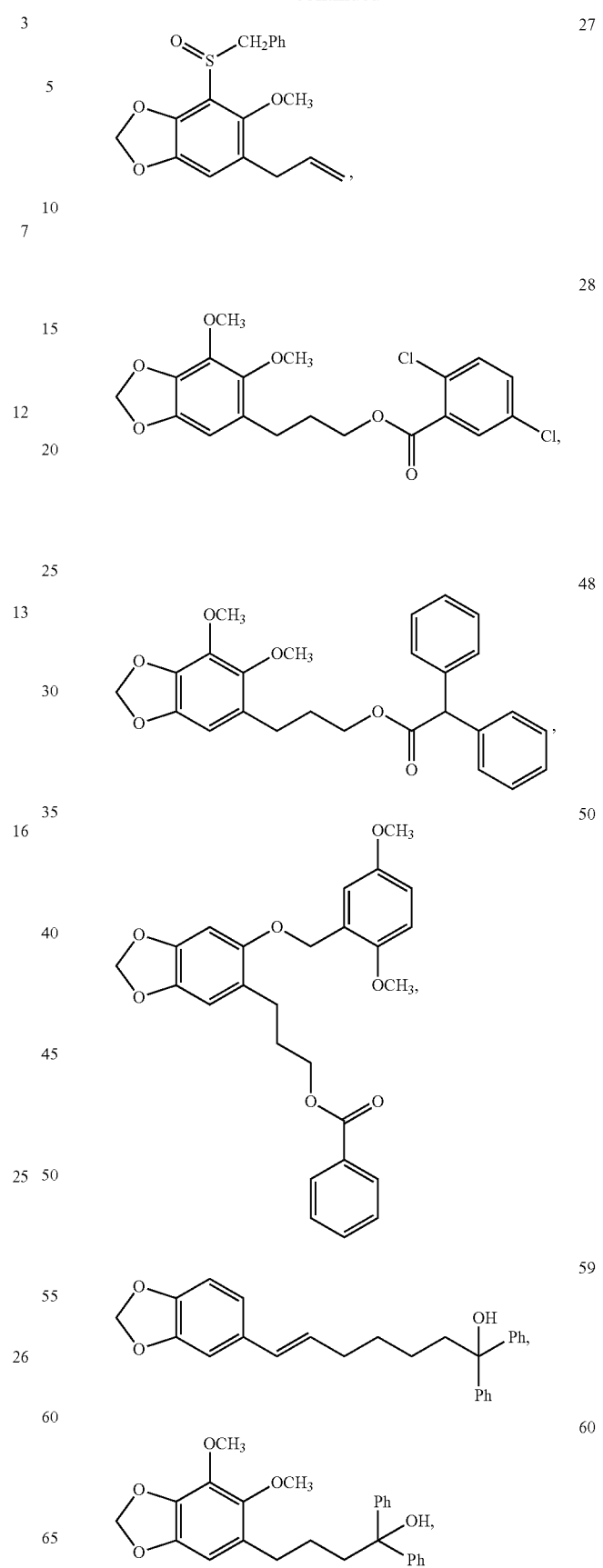

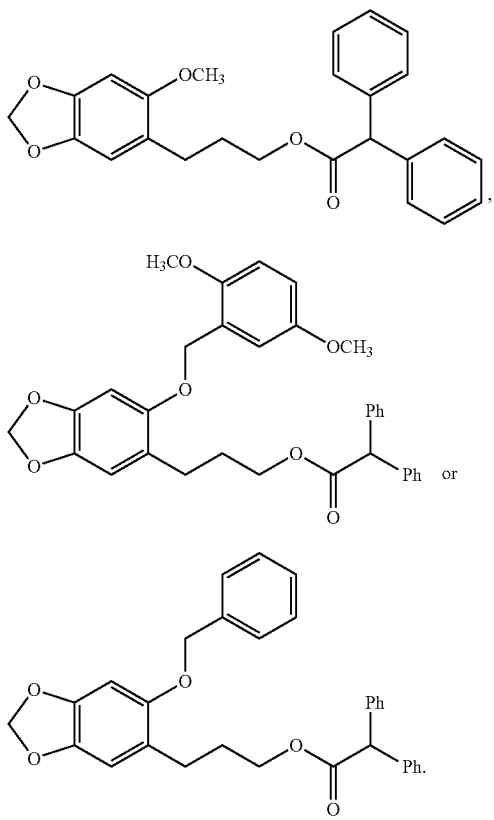

The present invention further provides methods for the use of a compound as described herein as a synergist. For instance, yet without wishing to be limiting in any way, the synergist may be a pharmaco-enhancer or a pesticide synergist.

Accordingly, there is further provided a method of increasing the efficacy and/or bioavailability of a pharmaceutically active agent. The method comprises administering a compound as described herein to a patient in need thereof together with said pharmaceutically active agent. In certain embodiments of this method, the pharmaceutically active agent is metabolized less quickly by a cytochrome P450 enzyme and the bioavailability of the active principle is increased. In specific embodiments, which are also non-limiting, the enzyme is the CYP3A4 enzyme. In addition, it is also to be understood that the compound may be administered prior to, subsequent to, or simultaneously with administration of the pharmaceutically active agent.

There is also provided herein a method of increasing the potency of a pesticide. This method comprises administering a compound as described herein to a pest or to a habitat thereof together with the pesticide. In certain non-limiting embodiments of this method the pesticide is metabolized by an insect cytochrome P450 enzyme, for example, a CYP6B8 enzyme. In addition, the compound may be administered prior to, subsequent to or simultaneously with the pesticide.

Also provided herein is a synergistic pesticidal composition comprising (a) at least one pesticidal compound, and (b) an amount, sufficient to increase the potency of the pesticide, of a pesticide. In a non-limiting embodiment, the pesticide may be an insecticide. For example, yet without wishing to be limiting in any way, the pesticide may be of the pyrethrin class and may further be useful for the control of an insect species such as coddling moth, flies, cockroaches, fire ants, *Tribolium* sp. and other stored product insects There is accordingly provided a method of combating pests which comprises applying to such pests or to a habitat thereof a pesticidally effective amount of a synergistic pesticidal composition as described herein.

There is further provided herein a synergistic pharmaceutical composition comprising (a) at least one pharmaceutically active agent, and (b) an amount, sufficient to increase the efficacy and/or bioavailability of the pharmaceutical active agent, of a compound as described herein.

Further embodiments and details of the invention are described below.

BRIEF DESCRIPTION OF THE DRAWINGS

These and other features of the invention will become more apparent from the following description in which reference is made to the appended drawings, wherein.

DETAILED DESCRIPTION

Figure 1:
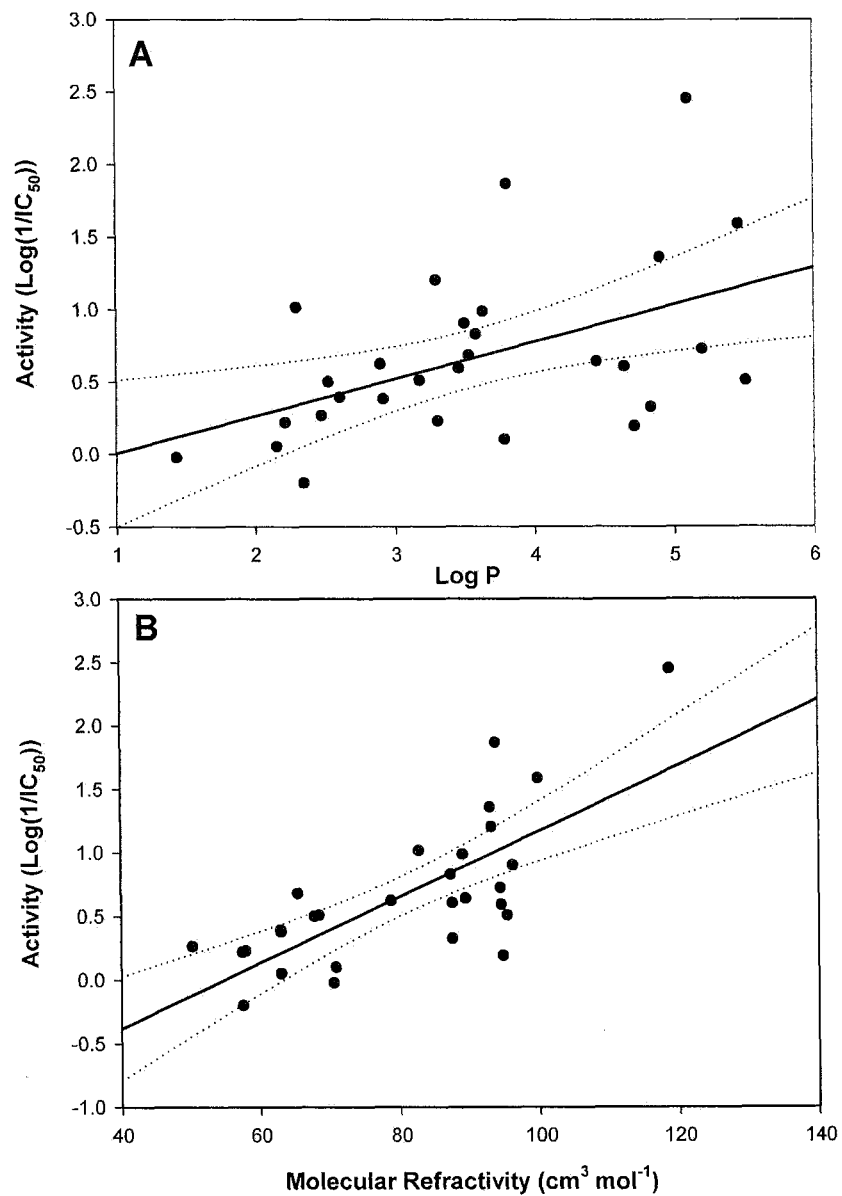
FIG. 1 shows plots of activity versus independent variables (Log P and MR). (A) Activity ($Log(1/IC_{50})$) versus Log P (Log partition coefficient), $R^2=0.24$, $p<0.05$; and (B) Activity ($Log(1/IC_{50})$) versus molecular refractivity (MR), $R^2=0.54$, $p<0.05$.

Described herein are derivatives of dillapiol, sesamol and related monolignans useful as synergists, including but not limited to pesticidal synergists and pharmaco-enhancers.

Use of these compounds as synergists can, in non-limiting embodiments, decrease the effective dosage of certain pesticides, drugs, or other bioactive compounds, and accordingly result in cost savings. In addition, by using these synergists in further non-limiting embodiments of the invention to enhance the effectiveness of otherwise toxic compounds, such as insecticides and other pesticides, application rates of these compounds can be lowered. A lower rate of insecticide application would have a significant environmental impact, and can further benefit workers and consumers through reduced exposure. Application at the same rate with these synergists may overcome resistance.

The compounds described can, in certain embodiments, be used as pesticide synergists, e.g. synergists of insecticides of the pyrethrin class. Accordingly, these compounds can be used in the control of a variety of insect species including, without limitation, coddling moth, flies, cockroaches, fire ants, and stored product insects such as *Tribolium*, etc.

The compounds described can also, in further embodiments, be used as a pharmaco-enhancer.

EXAMPLES

Example 1

CYP3A4 Inhibition and QSAR Modeling

A suite of dillapiol derivatives were synthesized and assayed for their capacity to inhibit human cytochrome CYP3A4. For each molecule, experimental $IC_{50}$ values for CYP3A4 inhibition were determined. These $IC_{50}$ values together with the log of the octanol-water partition coefficient (logP) and molecular refractivity (MR) are shown in Table 1, and were used as parameters to model a quantitative structure-activity relationship (QSAR). The resulting equations were used to guide the design of further derivatives with enhanced CYP3A4 inhibition.

TABLE 1
CYP3A4 IC$_{50}$ values, logP coefficients and molecular refractivity (MR) of selected dillapiol derivatives.
| Number | Compound | Log P | MR(cm3/mol) | IC$_{50}$ (mM) | Rel. Activity Dillapiol = 1.0 |
|---|---|---|---|---|---|
| dillapiol | 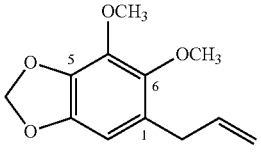 [SMILES: C=CCc1cc2c(c(OC)c1OC)OCO2] | 2.61 | 63.1 | 0.41 | 1.0 |
| 1) | 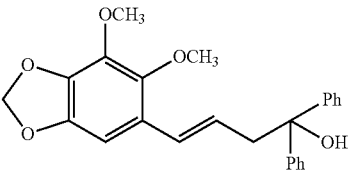 [SMILES: COc1c(/C=C/CC(O)(c2ccccc2)c2ccccc2)cc2c(c1OC)OCO2] | 5.11 | 119 | 0.0036 | 114 |
| 2) | 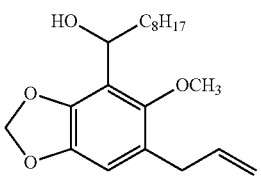 | 5.47 | 100 | 0.026 | 15 |
| 3) | 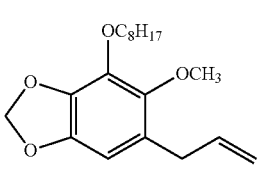 | 5.52 | 95.5 | 0.32 | 1.3 |
| 4) | 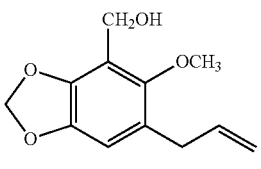 [SMILES: C=CCc1cc2c(c(CO)c1OC)OCO2] | 2.16 | 63.1 | 0.90 | 0.45 |
| 5) | 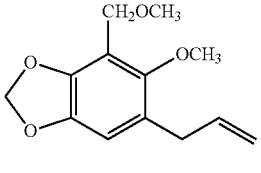 | 2.53 | 68 | 0.32 | 1.3 |
| 6) | 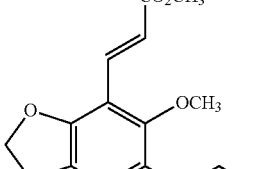 | 2.90 | 79 | 0.24 | 1.7 |
| 7) | 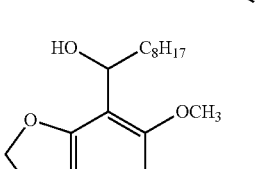 | 5.21 | 94.6 | 0.19 | 2.2 |

TABLE 1-continued
CYP3A4 IC$_{50}$ values, logP coefficients and molecular refractivity (MR) of selected dillapiol derivatives.
| Number | Compound | Log P | MR(cm3/mol) | IC$_{50}$ (mM) | Rel. Activity Dillapiol = 1.0 |
|---|---|---|---|---|---|
| 8) | 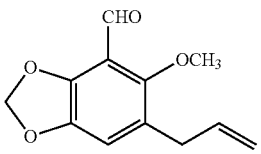 [SMILES: C=CCc1cc2c(c(C=O)c1OC)OCO2] | 2.22 | 58 | 0.62 | 0.66 |
| 9) | 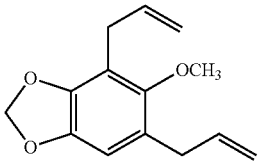 [SMILES: C=CCc1cc2c(c(CC=C)c1OC)OCO2] | 3.79 | 71 | 0.81 | 2.0 |
| 10) | 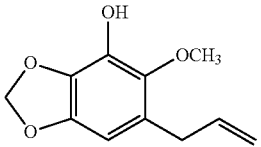 | 2.35 | 58 | 1.6 | 0.26 |
| 11) | 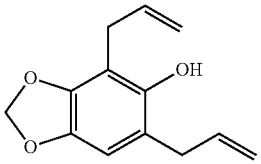 [SMILES: C=CCc1cc2c(c(CC=C)c1O)OCO2] | 3.53 | 66 | 0.21 | 1.9 |
| 12) | 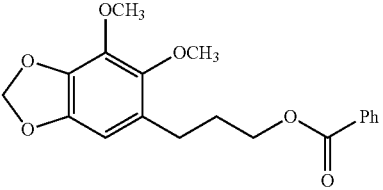 [SMILES: COc1c(CCCOC(=O)c2ccccc2)cc2c(c1OC)OCO2] | 3.81 | 94 | 0.014 | 29 |
| 13) | 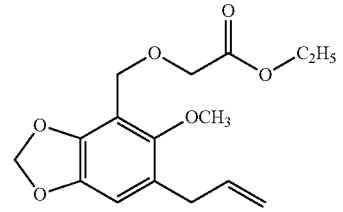 [SMILES: C=CCc1cc2c(c(COCC(=O)OCC)c1OC)OCO2] | 2.39 | 83 | 0.098 | 4.2 |
| 14) | 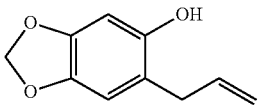 | 2.48 | 50 | 0.55 | 0.75 |
| 15) | 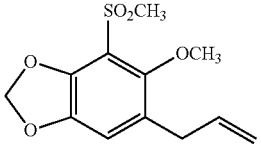 [SMILES: C=CCc1cc2c(c(S(C)(=O)=O)c1OC)OCO2] | 1.44 | 71 | 1.1 | 0.37 |

TABLE 1-continued
CYP3A4 IC$_{50}$ values, logP coefficients and molecular refractivity (MR) of selected dillapiol derivatives.
| Number | Compound | Log P | MR(cm3/mol) | IC$_{50}$ (mM) | Rel. Activity Dillapiol = 1.0 |
|---|---|---|---|---|---|
| 16) | 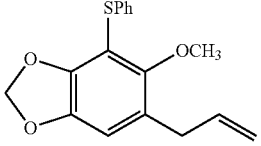 | 4.84 | 88 | 0.48 | 0.84 |
| 17) | 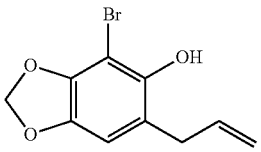 | 3.32 | 58 | 0.60 | 0.68 |
| 18) | 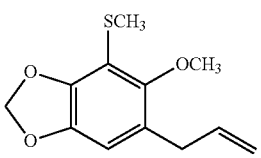 [SMILES: C=CCc1cc2c(c(SC)c1OC)OCO2] | 3.18 | 69 | 0.32 | 1.3 |
| 19) | 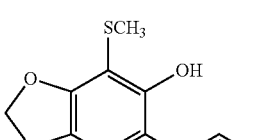 | 2.92 | 63 | 0.42 | 1.0 |
| 22) | 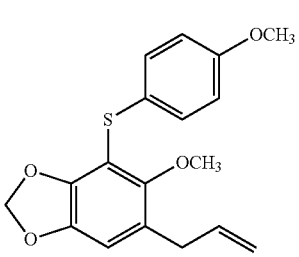 [SMILES: C=CCc1cc2c(c(Sc3ccc(OC)cc3)c1OC)OCO2] | 4.72 | 95 | 0.66 | 0.67 |
| 23) | 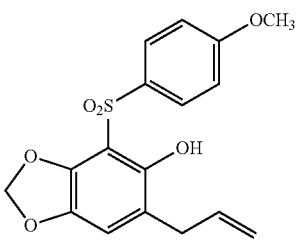 [SMILES: C=CCc1cc2c(c(S(=O)(=O)c3ccc(OC)cc3)c1O)OCO2] | 4.45 | 89 | 0.23 | 1.8 |
| 24) | 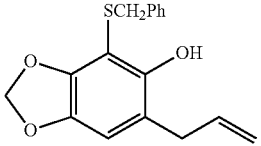 | 4.65 | 88 | 0.0.5 | 1.6 |
| 25) | 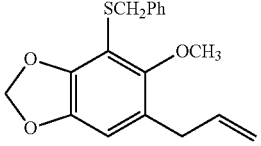 | 4.91 | 93 | 0.044 | 9.3 |

TABLE 1-continued

CYP3A4 IC$_{50}$ values, logP coefficients and molecular refractivity (MR) of selected dillapiol derivatives.

| Number | Compound | Log P | MR(cm3/mol) | IC$_{50}$ (mM) | Rel. Activity Dillapiol = 1.0 |
|---|---|---|---|---|---|
| 26) | | 3.58 | 87 | 0.15 | 2.7 |
| 27) | | 3.50 | 93 | 0.064 | 6.4 |

Several of these compounds show inhibition levels of 30 to more than 100 times greater than dillapiol itself. In particular, derivatives 1, 2, 12, 13, 25 and 27 have IC$_{50}$s which are at least four times lower than dillapiol; the most active compound 1, inhibits CYP3A4 100 times more strongly than dillapiol.

By analyzing this data, the inventors have developed a model to help further direct the design of derivatives that are likely to show increased inhibition of CYP3A4, and accordingly, an increased ability to enhance the activity of certain drugs and insecticides.

Introducing large substituents at the terminus of the allyl chain of dilapiol strongly enhances CYP inhibition. Thus, for example, the ester 12 and the alcohol 1 are 29 and 114 times more potent than dillapiol. Replacement of the C3 methoxy group by a nine carbon secondary alcohol resulting in 2 improved the inhibition by a factor of 15. The thioether 25 showed a 9-fold enhancement. The derivative 13, bearing a CH$_2$OCH$_2$CO$_2$C$_2$H$_5$ substituent at C5 inhibits the CYP3A4 enzyme 4.2 times more strongly than dillapiol. Most of the other derivatives prepared inhibited CYP3A4 to the same or similar extent as dillapiol. Typically a combination of a large substituent combined with a logP value of greater than 4 is required to give inhibition of CYP3A4 greater than by more than a factor of 2 relative to dillapiol.

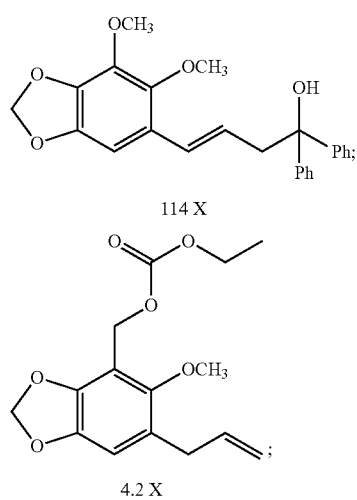

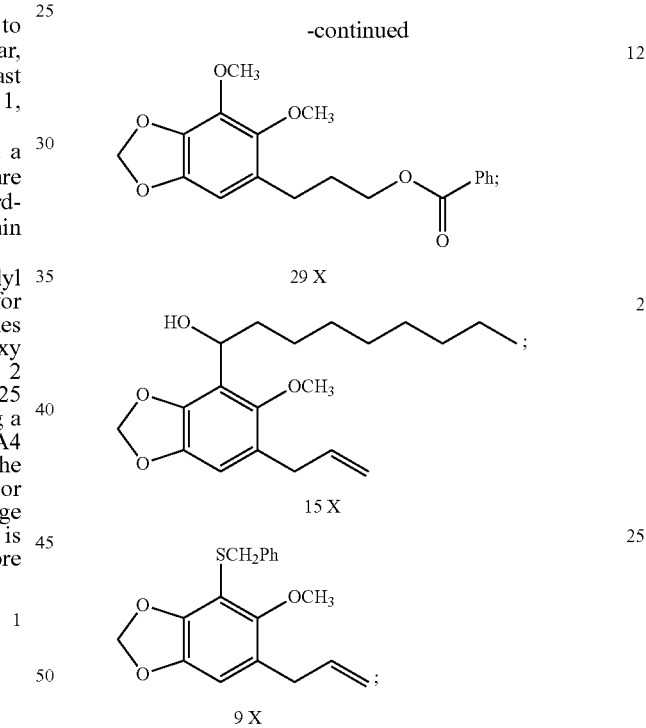

Although there are differences in human and insect protein sequences, the CYP3A4 enzyme of humans has the same mechanism of action and similar very broad substrate acceptance as CYP6B8 from the generalist insect herbivore *Helicoverpa zea*. Thus, inhibition of the human CYP3A4 enzyme is expected to be a predictor of inhibition of the CYP6B8 enzyme. Accordingly, compounds as described herein which are inhibitors of CYP3A4 are not only expected to act as pharmaco-enhancers in humans, but are also anticipated to be useful as pesticide synergists.

Data Analysis—QSAR:

Two series of forward and backward step-wise regressions were generated, one with logP as the independent variable and one with MR. For each molecule, experimentally determined $IC_{50}$ values (mM) were used as the dependent variable, expressed as activity, and calculated as $\log(1/IC_{50})$. A table of substitutions was prepared (Table 1) to describe the presence or absence of chemical substitutions at the 3 locations respective to the parent dillapiol molecule. The stepwise regressions were built by examining the extent to which the independent variables, logP or MR, accounted for the experimental activity observed, $\log(1/IC50)$), and was affected by the substitutions at each of the positions. In each case, the most parsimonious model associated with significant p-values and regression values greater than 0.5 were chosen. Kolmogorov-Schmirnoff and Levene's tests were used to verify the normality of distribution and the homogeneity of residual variance, respectively. All of the statistical values were calculated with S-PLUS software version 8.0 (Insightful Corp., Seattle, USA), the level of significance was set at $p<0.05$.

Development of the QSAR Model:

When Log P was plotted against activity a linear regression indicated that Log P is not a strong contributor to the activity observed, $R^2=0.24$, $p<0.05$ (FIG. 1A). In contrast, when MR was plotted against activity a moderate relationship was observed, $R^2=0.54$, $p<0.05$ (FIG. 1B). This indicates that 54% of the variability observed in the activity can be attributed to the molecular refractivity, a molecular character that can be understood simply as the bulkiness of a molecule. This suggests that the size and bulkiness of the molecule is a greater predictor of activity than lipophilicity. To examine the role that lipophilicity versus molecular refractivity has in observed activity, step-wise linear regressions were conducted.

When Log P was used as the independent variable and substitution information was taken into account, the equation associated with best model fit was:

$$\text{Activity}=0.1987 \log P + 1.3323\ C1 - 0.2315\ C6 - 0.0661, R^2=0.65, p<0.05 \quad \text{Equation 1}$$

Df Sum of Sq Mean Sq F Value Pr(F)

Log P 1 2.304909 2.304909 16.87009 0.0003759

C1 1 3.589059 3.589059 26.26904 0.0000270

C6 1 0.315536 0.315536 2.30947 0.1411352

Residuals 25 3.415674 0.136627

Figure 2:
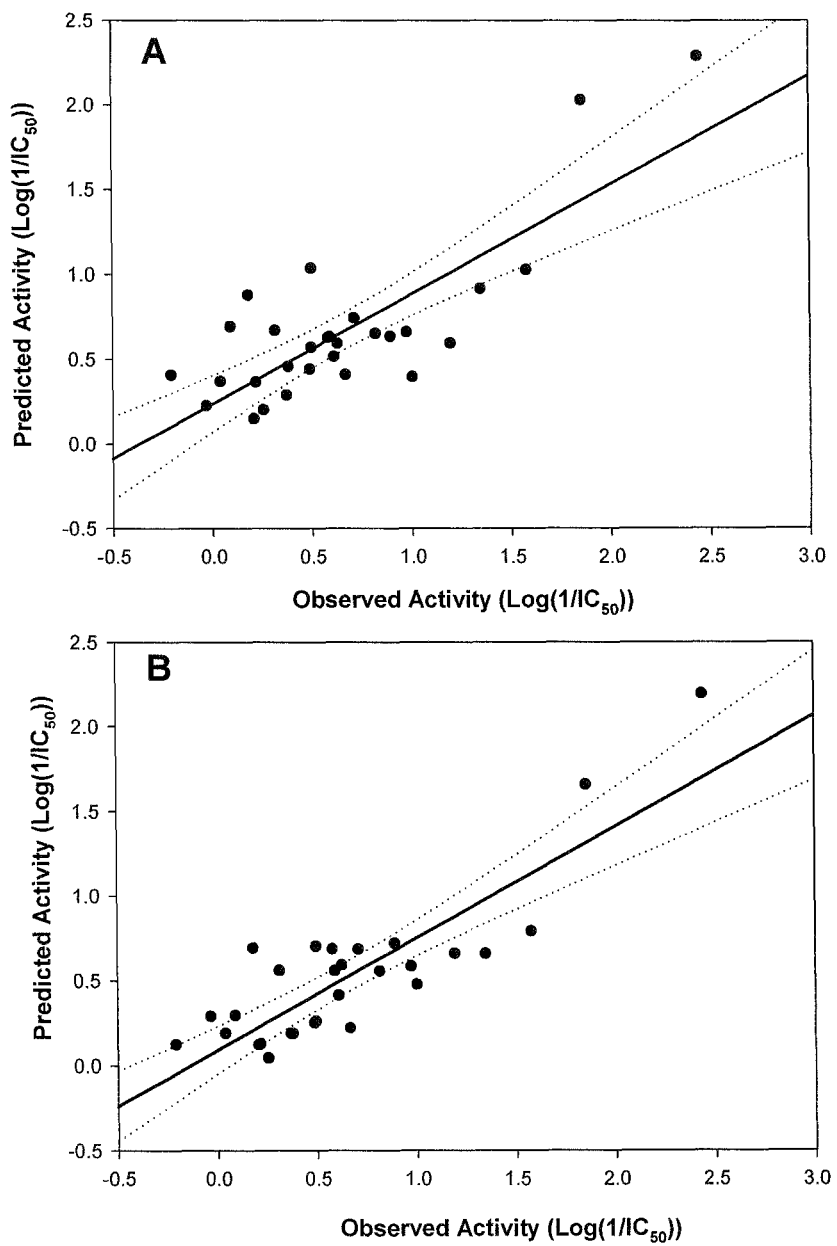
FIG. 2 shows the observed activity of dillapiol derivative molecules in the human CYP34A assay versus the predicted activity. (A) Predicted activity based on equation 1, with Log P as the independent variable and (B) Predicted activity based on equation 2, with MR as the independent variable.

The $R^2$ determined for this model indicates that the model accounts for 65% of the variability observed in the experimental data. This equation was used to calculate predicted activity values for the suite of molecules investigated and the values plotted against the observed experimental activity (FIG. 2A). An $R^2$ value of 0.645 was determined for this relationship, indicating that a higher degree of model fit was achieved when the substitutions were taken into account.

When MR was used as the independent variable and the substitution information was included in the step-wise linear regressions, the equation with the best model fit was:

$$\text{Activity}=0.0001(MR^2)+0.9851\ C1-0.2140, R^2=0.731, p<0.05 \quad \text{Equation 2}$$

Df Sum of Sq Mean Sq F Value Pr(F)

I(MR^2) 1 5.647685 5.647685 56.62671 0.0000000546

C1 1 1.384375 1.384375 13.88048 0.0009521616

Residuals 26 2.593119 0.099735

The $R^2$ determined for this equation indicates that the model accounts for 73% of the variability observed in the experimental data, an increase of 8% as compared to Equation 1 and further indicating that the molecular bulkiness is a greater predictor of activity in this assay than lipophilicity. This equation was used to calculate predicted activity values which were plotted against the observed activity values (FIG. 2B), where a $R^2$ value of 0.728 was determined, indicating a strong relationship.

Example 2

Experiments Using a Newer Enzyme Assay

In the second set of experiments, new CYP3A4 enzyme inhibition assays were conducted with a designed set of analogs and newer method described by Foster et al. (*J. Agric. Food Chem*, 2011, 59(9):5159-5163). This assay using the substrate dibenzylfluorescein (DBF) is considered more representative of CYP3A4 activity as compared to the benzyloxyresorufin assay previously used (Budzinski et al., 2000, Phytomedicine, 7(4):273-282).

Human CYP-Mediated Metabolism

Aliquots (10 μL) of stock solutions of the undiluted products were screened for their ability to inhibit CYP3A4 (BD-Gentest) metabolism of the non-fluorescent dibenzylfluorescein (DBF) substrates to the fluorescent metabolite using an in vitro fluorometric microtiter plate assay (CytoFluor Series 4000 multi-well plate reader). Briefly, assays were performed with 10 μL of product in clear-bottom, opaque-welled microtiter plates (96 well, Corning Costar). Control and control blank wells contained 5% ethanol, and test and test blank wells contained the product. All wells tested contained distilled water, β-nicotinamide adenine dinucleotide phosphate, reduced form (NADPH, Sigma Chemicals), and the enzyme substrate DBF (final concentration of 1 μM/well), for a total reaction volume of 200 μL. Control and test wells also contained live isozyme, within human microsomes, in phosphate buffer solution (PBS; 0.5 M, pH 7.4), and control blank and test blank wells contained denatured isoenzyme in PBS. Fluorescence was measured at 485 nm excitation and 530 nm emission, with a gain of 50.

The new bioassay results are shown in Table 2.

TABLE B

Activity of Dillapiol analogs, using a new CYP 3A4 bioassay described by Foster et al (2011). The Log P, MW and $IC_{50}$ values for each compound is shown.

| Compound | Log P | MW | $IC_{50}$ µM | $IC_{50}$ µg/mL | % Activity relative to dillapiol = 1 |
|---|---|---|---|---|---|
| 12 | 3.81 | 344 | 2.1 | 0.725 | 4.4 |
| 28 | 4.93 | 412 | 1.4 | 0.59 | 6.56 |
| 29 | 3.59 | 388 | 2.63 | 1.02 | 3.49 |
| 30 | 3.82 | 338 | 3.25 | 1.1 | 2.82 |
| 31 | 3.78 | 330 | 6.66 | 2.2 | 1.38 |

TABLE B-continued
Activity of Dillapiol analogs, using a new CYP 3A4 bioassay described by Foster et al (2011). The Log P, MW and IC$_{50}$ values for each compound is shown.
| Compound | Log P | MW | IC$_{50}$ μM | IC$_{50}$ μg/mL | % Activity relative to dillapiol = 1 |
|---|---|---|---|---|---|
| 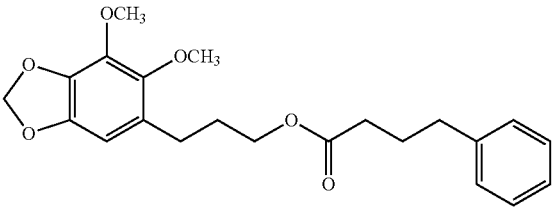 32 | 4.59 | 386 | 4.14 | 1.6 | 2.22 |
| 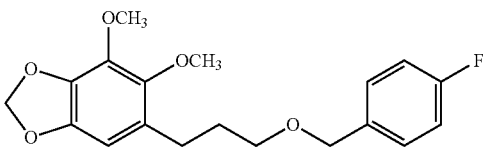 34 | 3.94 | 348 | 10.3 | 3.6 | 0.89 |
| 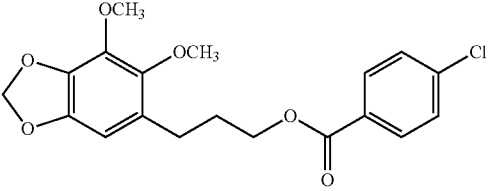 35 | 4.37 | 379 | 1.56 | 0.59 | 5.89 |
| 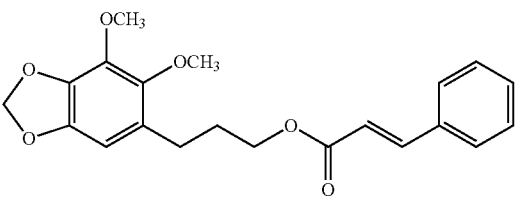 36 | 4.15 | 370 | 2.38 | 0.88 | 3.86 |
| 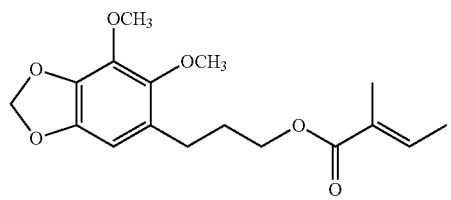 37 | 3.31 | 322 | 1.55 | 0.50 | 5.9 |

TABLE B-continued

Activity of Dillapiol analogs, using a new CYP 3A4 bioassay described by Foster et al (2011). The Log P, MW and IC$_{50}$ values for each compound is shown.

| Compound | Log P | MW | IC$_{50}$ μM | IC$_{50}$ μg/mL | % Activity relative to dillapiol = 1 |
|---|---|---|---|---|---|
| 38 | 1.91 | 282 | 9.22 | 2.6 | 1 |
| 39 | 4.37 | 379 | 5.27 | 1.998 | 1.75 |
| 40 | 4.28 | 340 | 4.73 | 1.61 | 1.94 |
| 41 | 4.22 | 328 | 2.15 | 0.705 | 4.27 |
| 42 | 4.47 | 268 | 1.44 | 0.385 | 6.37 |
| 43 | 3.01 | 194 | >26 | >5* | — |

TABLE B-continued

Activity of Dillapiol analogs, using a new CYP 3A4 bioassay described by Foster et al (2011). The Log P, MW and IC$_{50}$ values for each compound is shown.

| Compound | Log P | MW | IC$_{50}$ μM | IC$_{50}$ μg/mL | % Activity relative to dillapiol = 1 |
|---|---|---|---|---|---|
| 44 | 6.01 | 416 | 8 | 3.3 | 1.125 |
| 14 | 2.48 | 178 | >28 | >5* | — |
| 45 | 3.36 | 389 | >13 | >5* | — |
| 46 | 3.84 | 324 | 2.78 | 0.9 | 3.3 |
| 47 | 3.89 | 350 | 1.9 | 0.665 | 4.83 |

TABLE B-continued
Activity of Dillapiol analogs, using a new CYP 3A4 bioassay described by Foster et al (2011). The Log P, MW and IC$_{50}$ values for each compound is shown.
| Compound | Log P | MW | IC$_{50}$ μM | IC$_{50}$ μg/mL | % Activity relative to dillapiol = 1 |
|---|---|---|---|---|---|
| 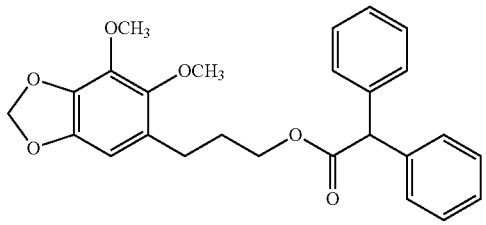 48 | 5.51 | 434 | 0.434 | 0.1885 | 21.15 |
| 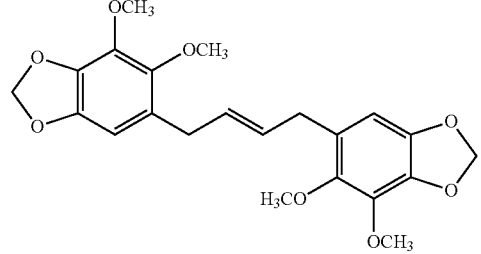 49 | 4.11 | 416 | 1.8 | 0.75 | 5.1 |
| 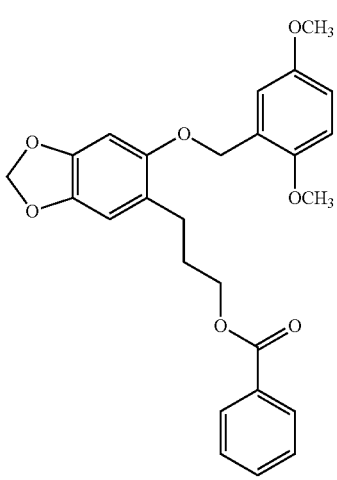 50 | 5.42 | 450 | 0.36 | 0.16 | 25.5 |
| 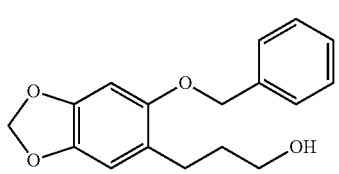 51 | 3.54 | 286 | 3 | 0.86 | 3 |

TABLE B-continued
Activity of Dillapiol analogs, using a new CYP 3A4 bioassay described by Foster et al (2011). The Log P, MW and IC$_{50}$ values for each compound is shown.
| Compound | Log P | MW | IC$_{50}$ μM | IC$_{50}$ μg/mL | % Activity relative to dillapiol = 1 |
|---|---|---|---|---|---|
| 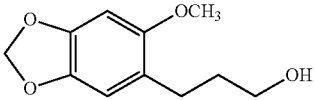 52 | 1.81 | 210 | 4.05 | 0.85 | 2.25 |
| 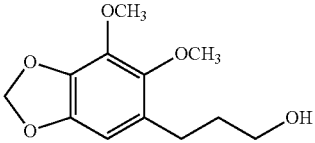 53 | 1.68 | 250 | 16 | 4 | 0.57 |
| 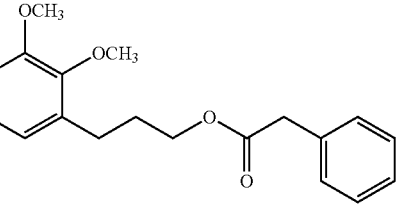 54 | 3.75 | 358 | 1.9 | 0.68 | 4.83 |
| 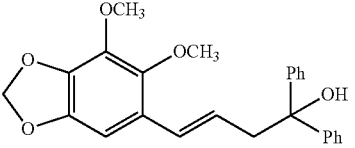 1 | 5.11 | 404 | 1.58 | 0.64 | 5.8 |
| 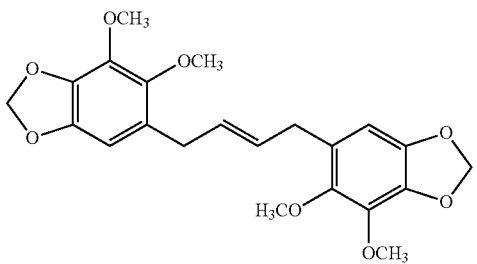 56 | 4.11 | 416 | 1.44 | 0.6 | 6.3 |
| 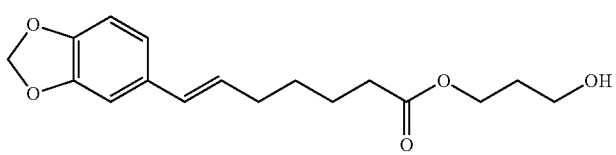 57 | 2.93 | 306 | 4.1 | 1.25 | 2.2 |

TABLE B-continued
Activity of Dillapiol analogs, using a new CYP 3A4 bioassay described by Foster et al (2011). The Log P, MW and IC$_{50}$ values for each compound is shown.
| Compound | Log P | MW | IC$_{50}$ μM | IC$_{50}$ μg/mL | % Activity relative to dillapiol = 1 |
|---|---|---|---|---|---|
| 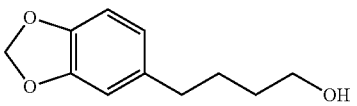 58 | 2.35 | 194 | >26 | >5 | / |
| 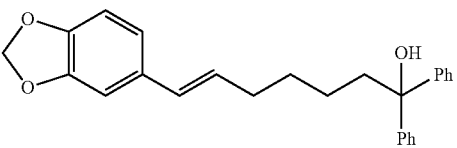 59 | 6.61 | 386 | 0.54 | 0.2 | 17 |
| 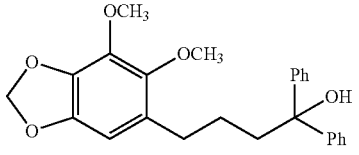 60 | 5.43 | 406 | 1.06 | 0.43 | 8.7 |
| 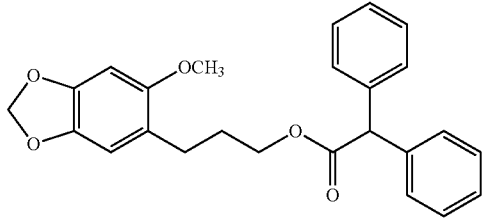 61 | 5.64 | 404 | 0.47 | 0.19 | 19.5 |
| 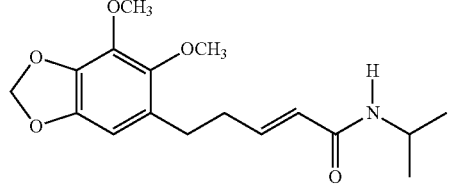 62 | 2.54 | 321 | 2.1 | 0.675 | 4.37 |
| 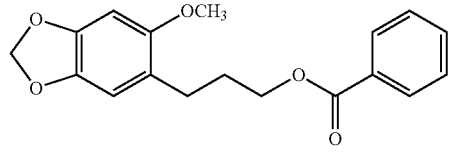 63 | 3.94 | 314 | 2.07 | 0.65 | 4.4 |

TABLE B-continued

Activity of Dillapiol analogs, using a new CYP 3A4 bioassay described by Foster et al (2011). The Log P, MW and $IC_{50}$ values for each compound is shown.

| Compound | Log P | MW | $IC_{50}$ µM | $IC_{50}$ µg/mL | % Activity relative to dillapiol = 1 |
|---|---|---|---|---|---|
| 64 | 2.74 | 192 | >16 | >5 | / |
| 65 | 2.08 | 254 | >20 | >5 | / |
| 66 | 3.08 | 248 | >>>20 | >>>5 | / |
| 67 | 2.00 | 254 | >20 | >5 | / |
| 68 | 2.1 | 254 | 11.6 | 2.95 | 0.8 |
| 69 | 7.1 | 540 | 0.23 | 0.12 | 41 |

TABLE B-continued

Activity of Dillapiol analogs, using a new CYP 3A4 bioassay described by Foster et al (2011). The Log P, MW and IC$_{50}$ values for each compound is shown.

| Compound | Log P | MW | IC$_{50}$ µM | IC$_{50}$ µg/mL | % Activity relative to dillapiol = 1 |
|---|---|---|---|---|---|
| 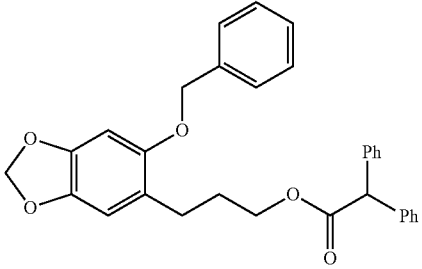 70 | 7.3 | 480 | 0.62 | 0.3 | 14 |
| 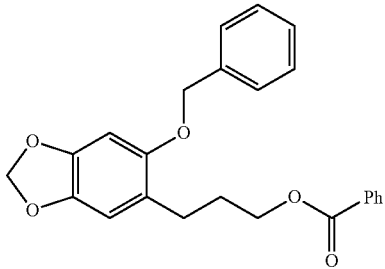 71 | 5.6 | 380 | 3.9 | 1.5 | 2.3 |
| 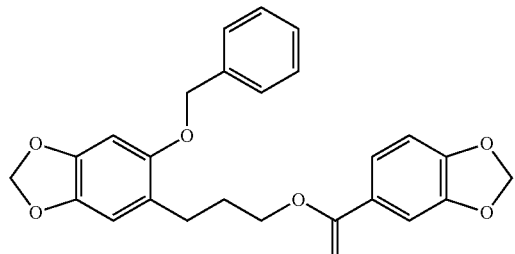 72 | 5.38 | 434 | 1.4 | 0.6 | 6.6 |
| Dillapiol 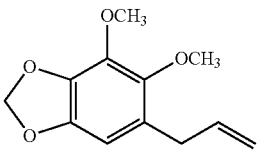 Chemical Formula: C$_{12}$H$_{14}$O$_4$ Molecular Weight: 222.24 | 2.61 | 222. | 9.18 | 2.1 | 1 |

The results shown in Table 2, although quantitatively somewhat different from those in Table 1 since they were obtained using a different assay, show that compounds common to both data sets show similar trends. Thus, the compounds 1 and 12 as shown in Tables 1 and 2, have increased inhibition of CYP3A4 compared to dillapiol. Additionally, the new bioassay revealed that increasing the size of the R$_4$ group in compounds having structures II, III, IV and V significantly increases the inhibition of human CYP3A4. The effect is strongest if there are non-hydrogen substituent groups to the carbonyl group of the ester. This is illustrated below for compounds belonging to the family II. The inhibition activity is given relative to dillapiol=1.

Similar trends are observed with compounds having formulae III, IV and V. This is illustrated with compounds 50, 61, 63, 69 and 70, below. For example 61 and 70 inhibited CYP3A4 19.5 and 4 fold, respectively more strongly than dillapiol.

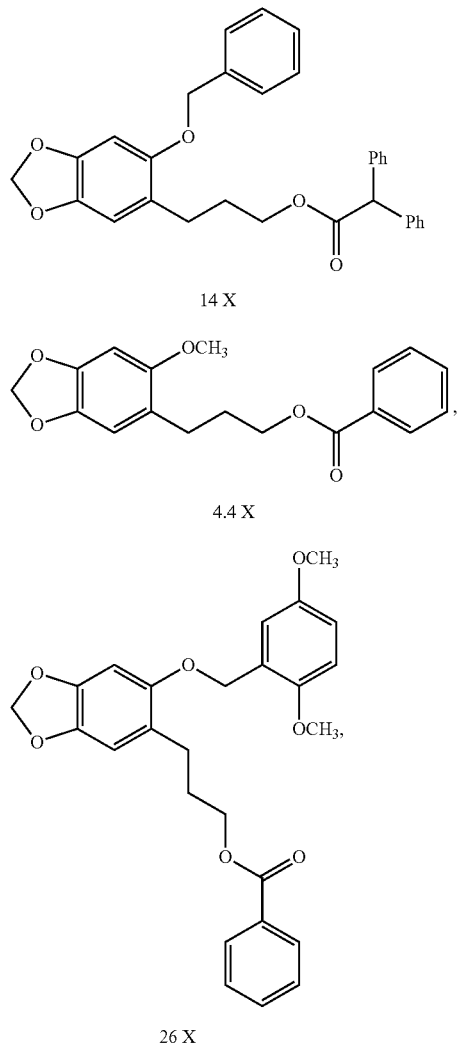

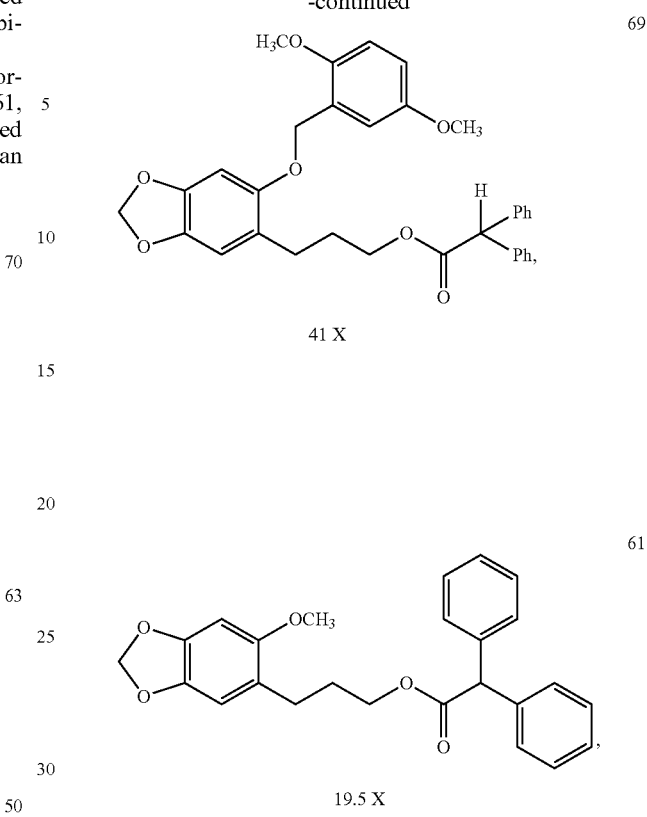

Analog Synthesis

The synthesis of certain compounds referred to herein has been described in S. Majerus, N. Alibhai, S. Tripathy and T. Durst. New Syntheses of Dillapiol [4,5 dimethoxy-6-(2-propenyl)-1,3-benzodioxole], its 4-Methylthio, and other Analogs. Can. J. Chem. 2001 and S. Majerus, M.Sc. University of Ottawa, 1997, or can be carried out using dillapiol, sesamol or a related lignan such as safrole as starting material and reactions known in the literature.

For example, esters 73 other than 12 can be synthesized from the alcohol 74, prepared from the hydroboration product of dillapiol. Ethers such as 75 are obtained by reacting 74 with typical alkylating agents. Compounds 76, related to 1 can be prepared by condensing the lithio derivative 76, from dillapiol and nBuLi with a variety of ketones and aldehydes and esters. The alcohol 78 serves as intermediate for the preparation of derivatives isomeric to 73 and 75. Urethanes, for example 79, can be prepared from 74.

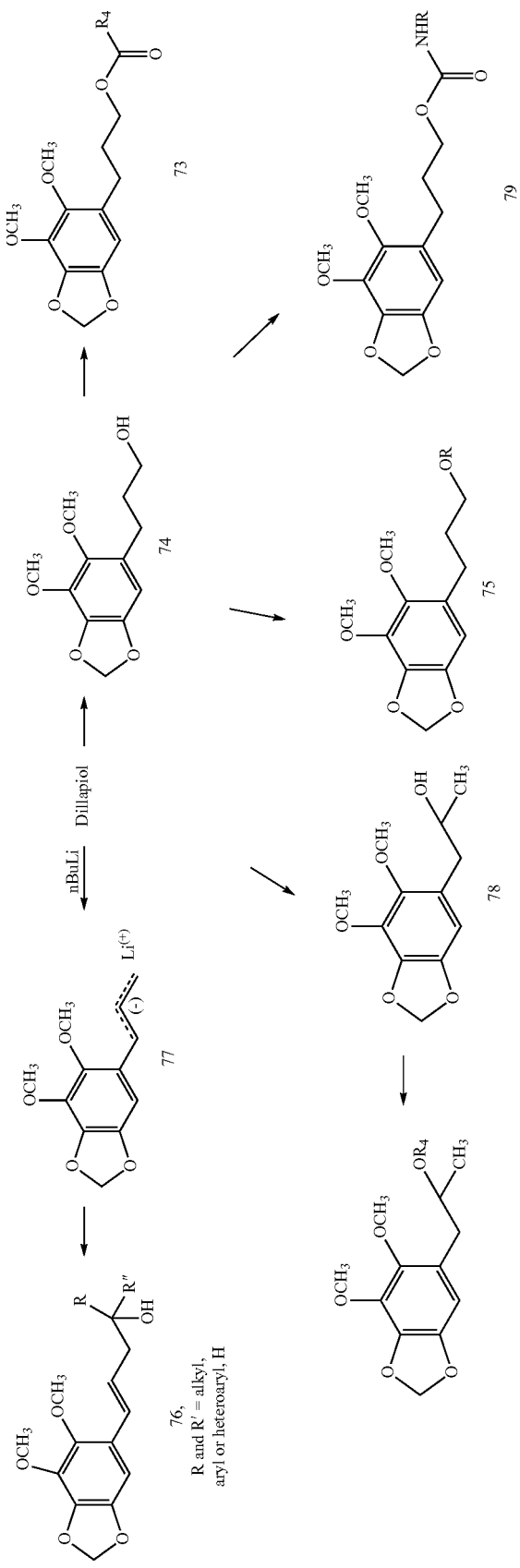

Metathesis of dillapiol gives 56, a compound which is 5.1 times more potent than dillapiol in inhibiting CYP3A4. Cross metathesis of dillapiol with acrylate derivatives yields a series of esters 80.

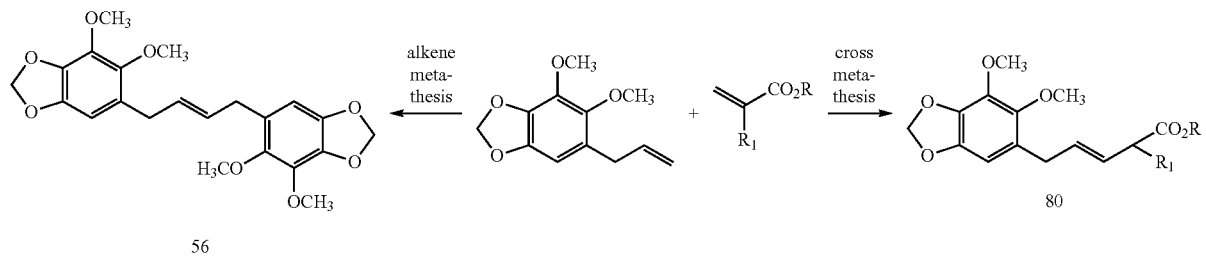

Derivatives have been prepared starting with sesamol to produce structures such as 81 which are analogs of excellent CYP inhibitors based on modification of dillapiol. Groups can be varied so that these types of compounds can be compared to compound 1. It is also possible to convert sesamol in four simple steps into the strong CYP3A4 inhibitors such as 50, 61, 63, 69 and 70 via the intermediate 52.

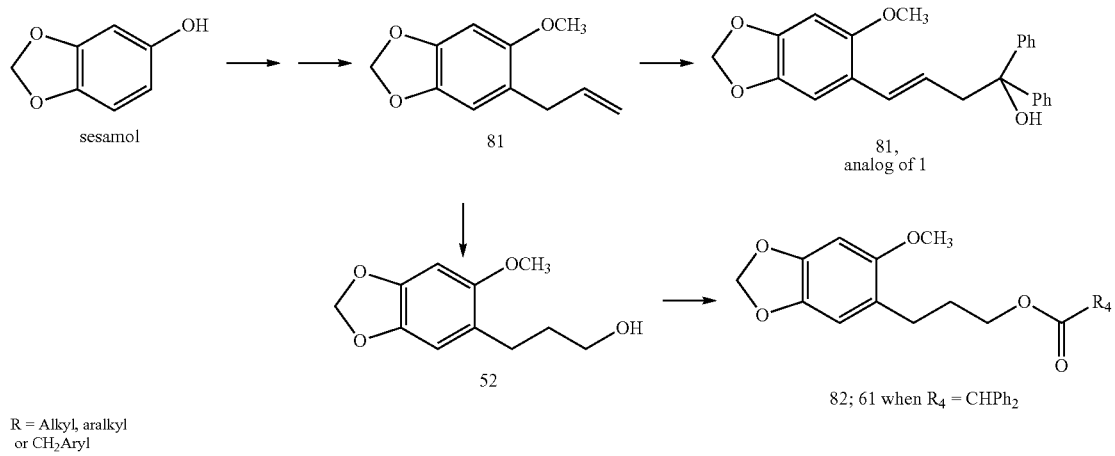

R = Alkyl, aralkyl or CH$_2$Aryl

Pyrogallol can readily lead to 83, analogs of the inhibitor 1 or for example 84, analogs of potent inhibitor 48 via the intermediate 85. This compound, obtained from pyrogallol in two steps, can be subjected to the other chemistry described for dillapiol and sesamol described above.

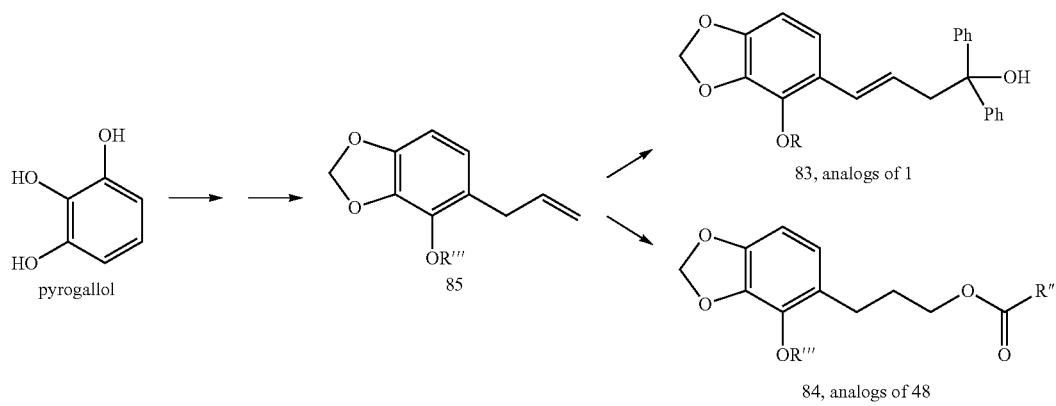

R = Alkyl, aralky or CH$_2$Aryl

Safrole can be used as a starting material. When subjected to the same types of reactions described for dillapiol and sesamol compounds such as 86 and 87 can be obtained.

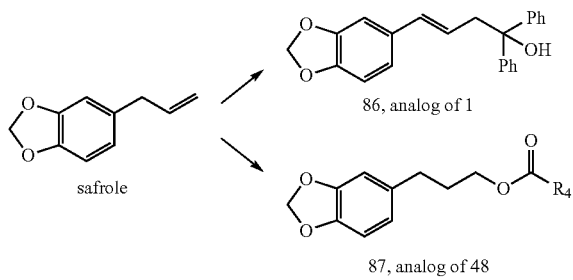

86, analog of 1

87, analog of 48

Starting with piperonal and using known chemistry (G. M. Strunz; H. Findlay. Phytochemistry, 39, 731, 1995; Tetrahedron, 732, 1994) the compounds we prepared via 57 the product 59 which inhibits CYP3A4 by a factor of 17 relative to dillapiol.

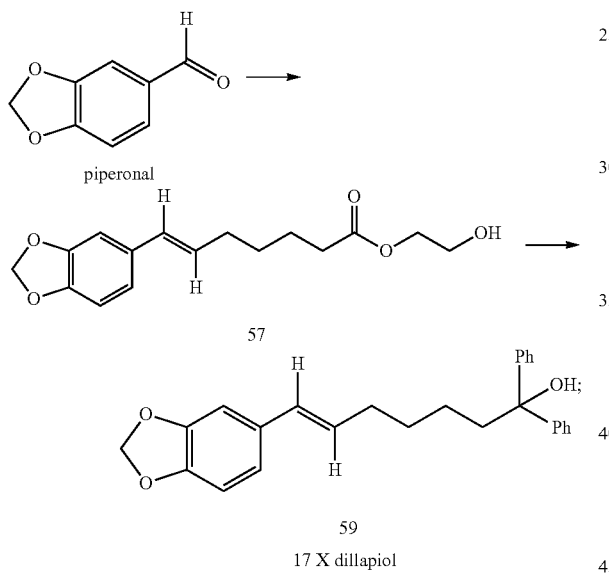

Treatment of dillapiol or ortho-allylated sesamol with $Br_2$ resulted in cyclization to a dihydrofuran intermediate 88 is converted either by reaction with $R_4CO_2$ K or by a two step process involving hydrolysis NaOH followed by acylation to compounds of compounds of the type V.

All of these compounds show significant inhibition of CYP3A4 and thus have potential as insecticide synergist and pharmaco-enhancers.

The chemistry used to prepare the various compounds is relatively simple and can be used to produce the specified compounds in an efficient and inexpensive manner starting with dillapiol, sesamol, pyrogallol, safrole or piperonal as precursor molecules. All of these starting materials either have or can be converted to compounds that have the important methylenedioxyphenyl structural unit.

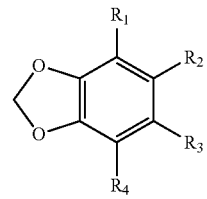

General Synthetic Procedures

As mentioned above, the key common reactions used for the preparation of the CYP3A4 inhibitors such as alkylation of a phenol, Claisen Rearrangement of allylated phenols to ortho-allyl phenols, hydroboration of a terminal alkene, acylation of an alcohol, alkene metathesis used are known. Thus not all of these are described herein. Several representative examples are given below.

Alkylation of Phenols, for Example 2-allyl-sesamol.

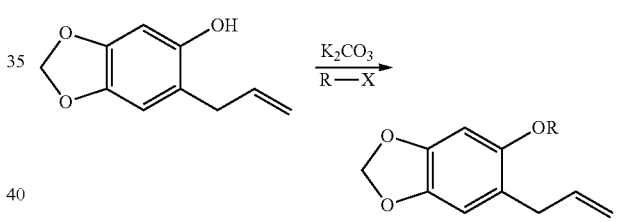

The phenol (1.0 eq) was dissolved in 5 mL of dry acetone. Potassium carbonate (1.5 eq) was added to this solution and the solution was stirred for 10 min at room temperature, after this time R—Cl (1.5 eq) was added. The reaction mixture was refluxed and the progress was monitored by TLC. Upon completion of the reaction the mixture was cooled to room temperature, the solvent was concentrated in vacuo. The remaining potassium carbonate was dissolved in water and the aqueous phase was extracted with ethyl acetate (3×40

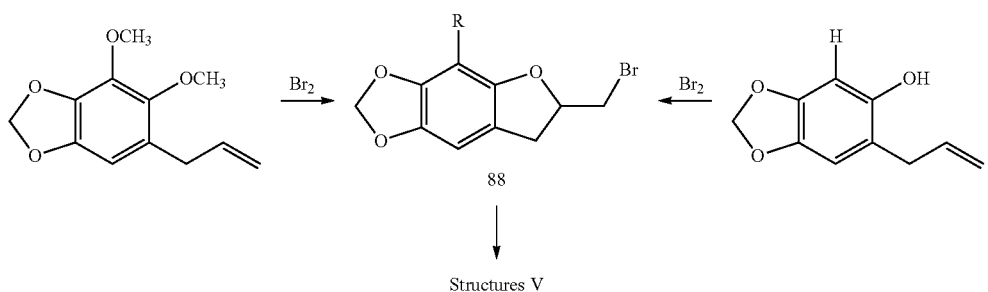

Structures V

Hydroboration of an allylbenzene

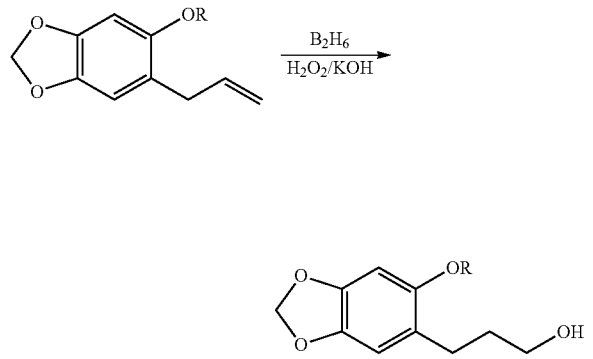

Borane/THF complex (1.5 eq) was added to a cooled (0° C.) solution of the allylbenzene (1.0 eq) in fresh distilled THF. The resulting reaction mixture was allowed to warm to RT and stirred over night. After this time the reaction was quenched with 10 mL of sodium hydroxide (3M), then 10 mL of $H_2O_2$ (30%) was added. The resulting mixture was extracted with ethyl acetate (3×20 mL). The organic extracts were combined and dried over magnesium sulfate, filtered and evaporated to dryness. Purification by flash chromatography (8:2, Hex:EtOAc) afford the desired alcohol.

Esterification with $R_4CO_2H$ and DCC (B. Neises, W. Steglich, *Angew. Chem. Int. Ed.,* 1978, 17, 522-524).

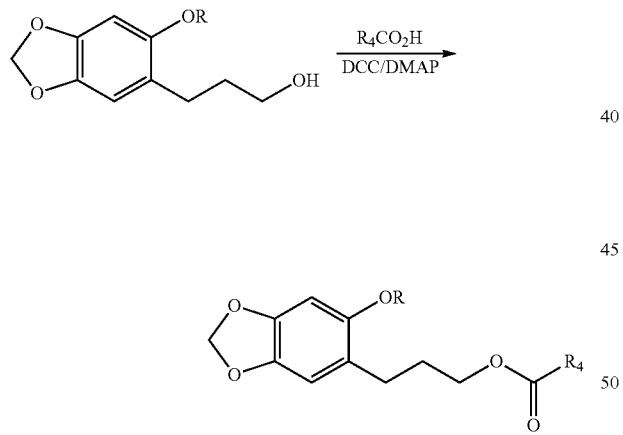

To a cooled solution (0° C.) of the corresponding carboxylic acid (1.0 eq), in dry DCM, 1.1 eq. of DCC (dicyclohexylcarbodiimide) and 10% mol of DMAP (4-dimethylaminopyridine) were added. The resulting solution was stirred for 5 min. after this time 2.0 eq. of the corresponding alcohol. The mixture was then allowed to warm to R.T. and was stirred until completion. The reaction was monitored by TLC. After the reaction is done, the reaction mixture is filtered to remove the urea formed in the process. The filtrate is then concentrated under vacuum. The resulting residue is re-suspended in DCM, if any more solid is present a second filtration most be carried out. The corresponding crudes were purified by flash chromatography, with different solvent systems of hexanes:ethyl acetate, to afford the corresponding ester.

An alternate method for forming these esters involves treatment of the alcohol with an acid chloride in DCM in the presence of a tertiary amine such as triethylamine.

Preparation of Compound 1.

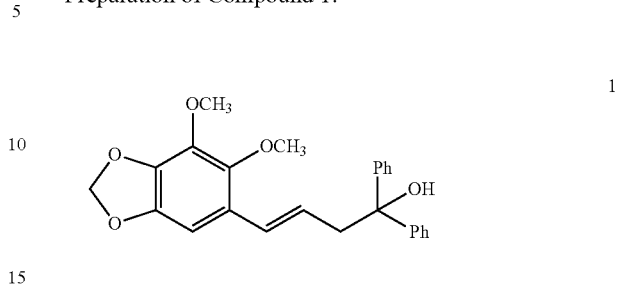

To a cooled (−78° C.) solution of dillapiol (0.5 g, 2.25 mmol) in dry THF (10 mL) was added dropwise 1.2 eq of n-BuLi (1.25 mL, 2.0M). The reaction mixture was stirred for 30 min, and then the reaction was allowed to warm up to 0.0 and kept there for another 30 min. After this time the reaction mixture was cooled to −78.0 for 5 minutes and then 1.3 eq of the corresponding ketone (0.25 g, 1.4 mmol) was added. The resulting mixture was stirred for 5 minutes. The reaction mixture was quenched using saturated $NH_4Cl$ solution (3 mL) and the aqueous phase was extracted with $Et_2O$ (3×20 mL). The organic phase was dried over $MgSO_4$, filtered and concentrated in vacuo to provide compound 1 after purification by column chromatography.

Characterization of Compounds.

All compounds produced had greater than 95% purity as judged by a combination of $^1H$ and $^{13}C$ NMR, and analytical thin layer chromatography. The NMR data of known compounds were compared with literature values. New structures were also characterized using High Resolution Mass Spectrometry [HRMS] as a measure of composition. The relative simplicity of most of the compounds combined with the synthetic procedures used allows one to assign structures with very high levels of confidence.

Several representative examples of NMR data are shown below.

Compound 1

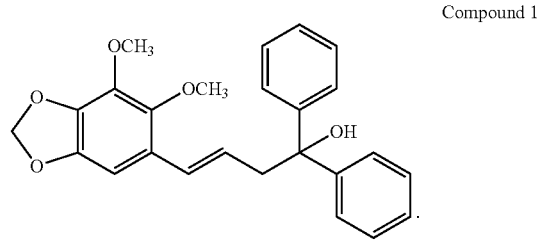 [SMILES: COc1c(/C=C/CC(O)(c2ccccc2)c2ccccc2)cc2c(c1OC)OCO2]

$H^1$ NMR δ 2.57 (s, 1H), 3.21 (dd, 2H, J: 7.3, 1.1 Hz), 3.66 (s, 3H), 3.98 (s, 3H), 5.84 (s, 2H), 5.85-5.90 (m, 1H), 6.45 (s, 1H), 6.74 (d, 1H, J: 16.0 Hz), 7.20-7.23 (m, 2H), 7.29-7.32 (m, 4H), 7.45-7.47 (m, 4H)

$^{13}C$ NMR δ 46.2, 60.0, 61.5, 77.4, 98.6, 101.3, 124.0, 124.2, 126.1, 126.9, 128.2, 129.2, 137.1, 137.5, 144.5, 145.0, 146.6

Compound 48

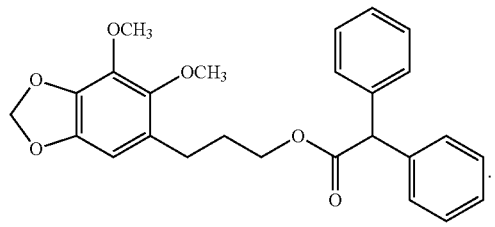

H$^1$ NMR δ, 1.87 (q, 2H, J$_1$:6.4 Hz) 2.51 (t, 2H, J: 7.3 Hz), 3.70 (s, 3H), 4.01 (s, 3H), 4.17 (t, 2H, J:6.5 Hz), 5.05 (s, 1H), 5.88 (s, 2H), 7.26-7.35 (m, 10H)

$^{13}$C NMR δ 26.32, 29.56, 57.21, 59.87, 61.10, 64.61, 101.06, 102.57, 126.49, 126.95, 127.20, 127.51, 128.45, 128.54, 128.59, 135.82, 137.58, 138.69, 144.35, 144.41, 172.43

Compound 61

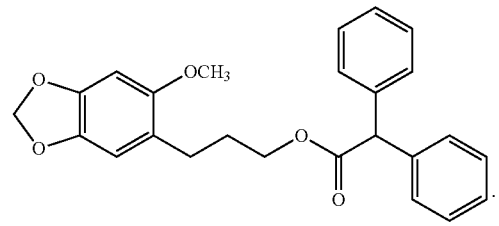

H$^1$ NMR δ, 1.84 (q, 2H, J$_1$:6.5 Hz), 2.49 (t, 2H, J: 7.2 Hz), 3.68 (s, 3H), 4.13 (t, 2H, J: 6.6), 5.02 (s, 1H), 5.86 (s, 2H), 6.46 (s, 2H), 7.23-7.32 (m, 10H)

$^{13}$C NMR δ 26.47, 28.92, 56.20, 57.24, 64.73, 94.59, 100.89, 109.80, 121.52, 127.20, 128.55, 128.62, 138.76, 140.66, 146.20, 152.25, 172.46

Compound 70

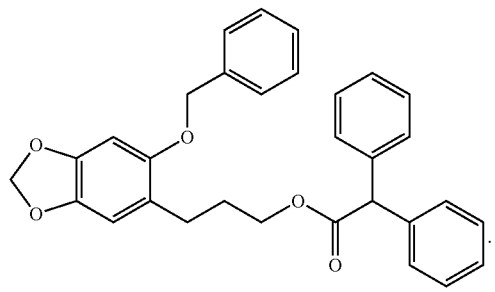

H$^1$ NMR δ 1.86 (q, 2H, J$_1$:6.5 Hz) 2.54 (t, 2H, J:6.5 Hz) 4.9 (s, 2H) 4.98 (s, 1H) 5.86 (s, 2H) 6.47 (s, 1H) 6.51 (s, 1H) 7.24-7.36 (m, 15H)

$^{13}$C NMR δ 26.7, 28.94, 57.20, 64.77, 71.13, 96.21, 100.98, 109.87, 122.18, 127.14, 127.24, 127.39, 127.42, 127.72, 127.86, 128.34, 128.37, 128.49, 128.59, 128.65, 129.04, 129.12, 137.25, 138.77, 141.08, 146.18, 151.21, 172.53

Compound 47

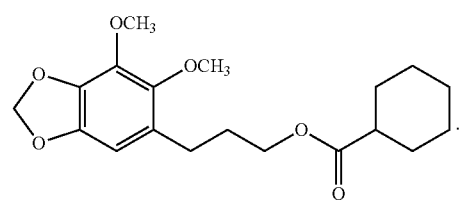

H$^1$ NMR δ, 1.18-1.50 (m, 5H), 1.61-1.66 (m, 1H), 1.71-1.93 (m, 6H), 2.25-2.33 (m, 1H), 2.58 (t, 2H, J:7.5 Hz), 3.75 (s, 3H), 4.01 (s, 3H), 4.07 (t, 2H, J:6.5 Hz), 5.87 (s, 2H), 6.32 (s, 1H).

$^{13}$C NMR δ 25.44, 25.75, 26.39, 29.02, 29.76, 43.24, 59.88, 61.16, 63.57, 101.04, 102.53, 127.21, 135.79, 137.61, 144.36, 144.47, 176.09

Compound 46

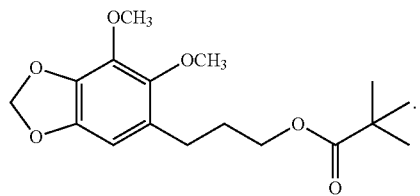

H$^1$ NMR δ 1.20 (s, 9H), 1.86 (q, 2H, J$_1$:6.3 Hz) 2.58 (t, 2H, J:7.5 Hz,) 3.75 (s, 3H,) 4.00 (s, 3H) 4.06 (t, 2H, J:6.4 Hz), 5.87 (s, 1H), 6.31 (s, 1H).

$^{13}$C NMR δ 26.38, 27.16, 29.80, 38.70, 59.85, 61.12, 63.73, 101.02, 102.50, 127.19, 135.76, 137.60, 144.31, 144.46, 178.47

Compound 69

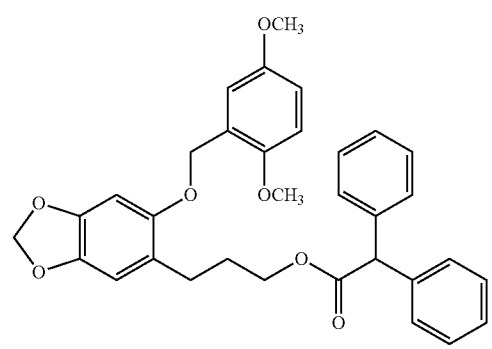

H$^1$ NMR δ, 1.90 (q, 2H, J$_1$:6.5 Hz), 2.57 (t, 2H, J: 7.2 Hz), 3.71 (s, 3H), 3.78 (s, 3H), 4.14 (t, 2H, J: 6.5), 4.97 (s, 2H), 5.01 (s, 1H), 5.85 (s, 2H), 6.47 (s, 1H), 6.56 (s, 1H), 7.01 (s, 1H), 7.22-7.33 (m, 10H)

$^{13}$C NMR δ 26.47, 28.92, 56.20, 57.24, 64.73, 94.59, 100.89, 109.80, 121.52, 127.20, 128.55, 128.62, 138.76, 140.66, 146.20, 152.25, 172.46

Compound 65

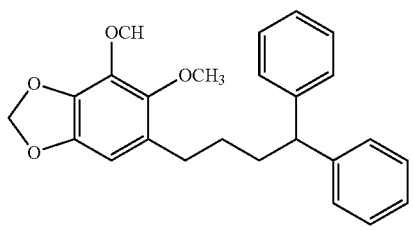

H¹ NMR δ, 1.49 (t, 2H, J=7.8 Hz), 2.53 (t, 2H, J: 7.72 Hz), 3.659 (s, 3H), 3.89 (t, 1H, J:7.9 Hz), 3.97 (s, 3H), 5.84 (s, 2H), 6.25 (s, 1H), 7.11-7.126 (m, 10H).

Compound 56

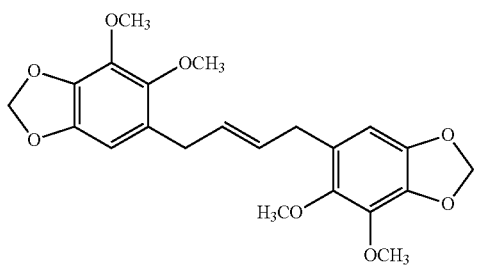

H¹ NMR δ, 3.26 (d, 2H, J=5.0 Hz), 3.26 (d, 2H, J=3.26 Hz), 4.01 (s, 6H), 5.55-5.58 (m, 2H), 5.88 (s, 4H), 6.34 (s, 2H).

All publications, patent applications and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A compound of formula I:

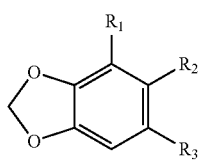

wherein

R₁ is H or OCH₃;

R₂ is H, OCH₃, OCH₂Ph, or OCH₂R wherein R is a benzene ring substituted with one or more of F, Cl Br, methyl, or methoxy;

R₃ is a structure of the following type

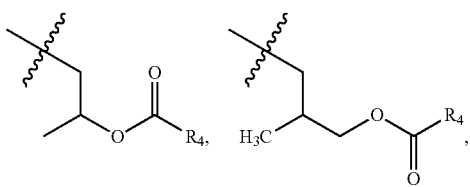

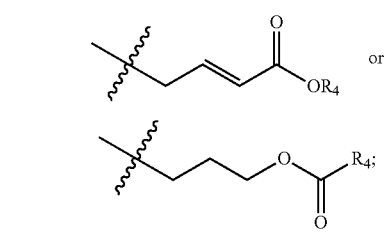

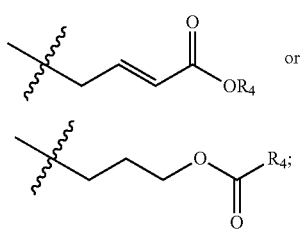

R₄ is CHAr₂, in which aryl (Ar) is unsubstituted phenyl (Ph) or Ph mono or di-substituted with a halogen, CH₃ or OCH₃, or a.

2. The compound of claim 1, wherein the compound is of the formula:

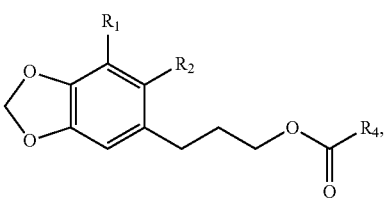

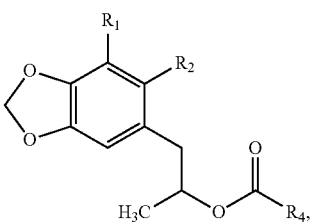

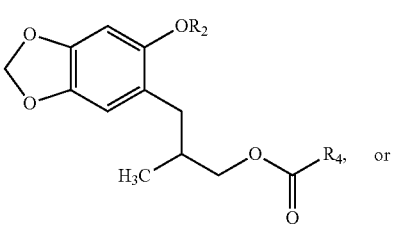

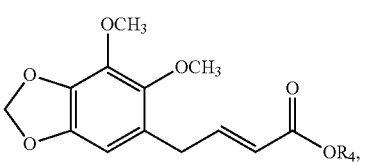

wherein R₁, R₂ and R₄ are as defined in claim 1.

3. The compound of claim 1 wherein the compound is:

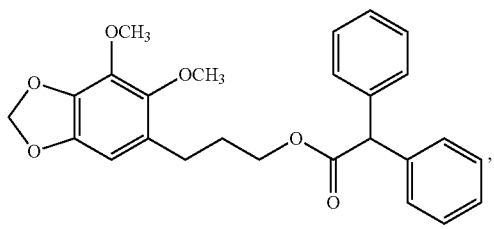, 48

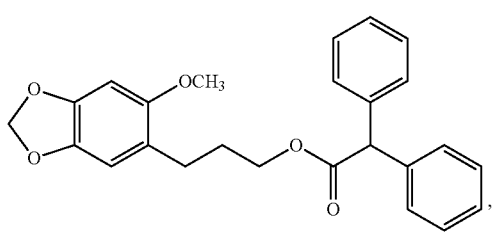, 61

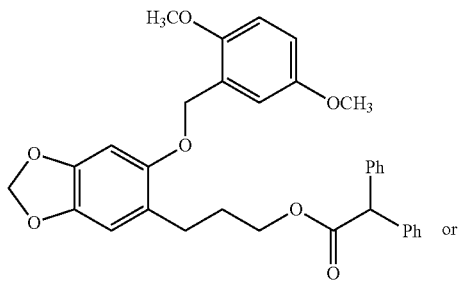 or, 69

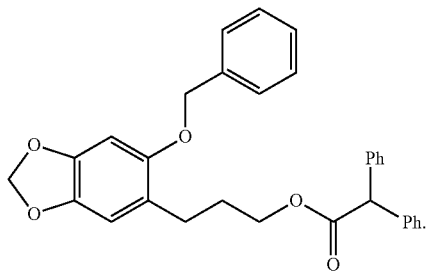. 70

4. The compound of claim 1, wherein the halogen is Cl or F.

5. A method of increasing the efficacy and/or bioavailability of a pharmaceutically active agent comprising administering a compound of claim 1 to a patient in need thereof together with said pharmaceutically active agent, in an amount effective to increase the efficacy and/or bioavailability of said pharmaceutically active agent.

6. The method of claim 5, wherein said compound is administered prior to, subsequent to, or simultaneously with said pharmaceutically active agent.

7. A method of increasing the potency of a pesticide comprising administering a compound of claim 1 to a pest or to a habitat thereof together with said pesticide, in an amount effective to increase the potency of said pesticide wherein said pesticide is metabolized by a cytochrome P450 6B8 (CYP6B8) enzyme.

8. The method of claim 7, wherein said compound is administered prior to, subsequent to, or simultaneously with said pesticide.

9. A synergistic pesticidal composition comprising (a) at least one pesticidal compound, and (b) an amount, sufficient to increase the potency of said pesticide, of a compound of claim 1 wherein said pesticidal compound is metabolized by a cytochrome P450 6B8 (CYP6B8) enzyme.

10. The composition of claim 9 wherein said pesticide is an insecticide.

11. The composition of claim 10, wherein said insecticide is of the pyrethrin class.

12. The composition of claim 10, wherein said composition is for the control of an insect species selected from the group consisting of coddling moth, flies, cockroaches, fire ants, *Tribolium* sp. and other stored product insects.

13. A method of combating pests which comprises applying to such pests or to a habitat thereof a pesticidally effective amount of a composition according to claim 9.

14. A synergistic pharmaceutical composition comprising (a) at least one pharmaceutically active agent, and (b) an amount, sufficient to increase the efficacy and/or bioavailability of said pharmaceutical active agent, of a compound of claim 1 wherein said pharmaceutically active agent is metabolized by a human cytochrome P450 3A4 (CYP3A4) enzyme.

* * * * *